US008473024B2

(12) United States Patent  
Causevic et al.

(10) Patent No.: US 8,473,024 B2
(45) Date of Patent: Jun. 25, 2013

(54) FLEXIBLE HEADSET FOR SENSING BRAIN ELECTRICAL ACTIVITY (75) Inventors: Elvir Causevic, New York, NY (US); Richard Comrie Watt, Greenwich, CT (US); Craig Anderson, Chicago, IL (US); Martin Rathgeber, Chicago, IL (US)

(73) Assignee: Brainscope Company, Inc., Bethesda, MD (US)

( * ) Notice: Subject to any disclaimer, the term of this patent is extended or adjusted under 35 U.S.C. 154(b) by 1054 days.

(21) Appl. No.: 12/190,232

(22) Filed: Aug. 12, 2008

(65) Prior Publication Data

US 2010/0041962 A1  Feb. 18, 2010

(51) Int. Cl.
*A61B 5/0478* (2006.01)
*A61B 5/0484* (2006.01)

(52) U.S. Cl.
USPC .................... 600/383; 600/393; 600/545

(58) Field of Classification Search
USPC .................... 600/383, 390, 393, 544–545
See application file for complete search history.

(56) References Cited

U.S. PATENT DOCUMENTS

| 5,341,806 | A | * | 8/1994 | Gadsby et al. | 600/393 |
|---|---|---|---|---|---|
| 5,479,934 | A | * | 1/1996 | Imran | 600/544 |
| 5,800,351 | A | | 9/1998 | Mann | |
| 6,077,237 | A | * | 6/2000 | Campbell et al. | 600/587 |
| 6,128,521 | A | | 10/2000 | Marro et al. | |
| 6,640,130 | B1 | * | 10/2003 | Freeman et al. | 600/474 |
| 7,206,630 | B1 | * | 4/2007 | Tarler | 600/509 |
| 7,299,088 | B1 | | 11/2007 | Thakor et al. | |
| D603,051 | S | * | 10/2009 | Causevic et al. | D24/187 |
| D641,886 | S | * | 7/2011 | Causevic et al. | D24/187 |
| D647,208 | S | * | 10/2011 | Rothman et al. | D24/187 |
| 8,391,948 | B2 | * | 3/2013 | Causevic et al. | 600/383 |
| 2004/0073129 | A1 | * | 4/2004 | Caldwell et al. | 600/544 |
| 2004/0193068 | A1 | * | 9/2004 | Burton et al. | 600/544 |
| 2005/0059899 | A1 | * | 3/2005 | Merilainen et al. | 600/544 |
| 2005/0107716 | A1 | | 5/2005 | Eaton et al. | |
| 2007/0032737 | A1 | | 2/2007 | Causevic et al. | |
| 2007/0191727 | A1 | * | 8/2007 | Fadem | 600/544 |
| 2008/0091090 | A1 | * | 4/2008 | Guillory et al. | 600/301 |
| 2009/0247894 | A1 | * | 10/2009 | Causevic | 600/544 |

OTHER PUBLICATIONS

Chiappa Evoked Potentials in Clinical Medicine, 3rd Edition; Lippencott-Raven (1997) p. 188.*
Stretchable and Elastic Electronics and Sensor Circuits, last updated Nov. 7, 2007, http: //tfcg.elis.ugent.be/projects/stretchable.html, pp. 1-4.
"2006-SEDline Brain-Function Monitoring System," last updated Jan. 20, 2008, http://www.chemilab.net/web/proiects/21-embedded/267-2006sedline.html, pp. 1-3.

(Continued)

*Primary Examiner* — Lee S Cohen
*Assistant Examiner* — Erin M Cardinal
(74) *Attorney, Agent, or Firm* — Finnegan, Henderson, Farabow, Garrett & Dunner LLP (57) ABSTRACT

A headset for detecting brain electrical activity is disclosed. The headset may have a flexible band having a first end and a second end. The flexible band may have at least one expansible region permitting a distance between the first end and the second end to selectably vary. The headset may also have flexible circuitry in the flexible band. The flexible circuitry may be operatively connected to at least one sensor configured to sense brain electrical activity. The headset may further have a stimulus emitter coupled to the flexible band.

55 Claims, 6 Drawing Sheets

OTHER PUBLICATIONS

"SEDLine™ Brain-Function Monitoring System," printed Feb. 27, 2008, http://www.hospira.com/Products/SEDline.aspx, pp. 1-2.

"PSA 4000 Brain-Function Monitoring System," printed Feb. 27, 2008, http://www.hospira.com/Products/PSA4000.aspx, pp. 1-2.

"Is the Patient State Analyzer with the PSArray$^2$ a Cost-Effective Alternative to the Bispectral Index Monitor During the Perioperative Period?" Paul F. White, PhD, MD, Fanzca, Jun Tang, MD, Hong Ma, MD, Ronald H. Wender, MD, Alexander Sloninsky, MD, and Robert Kariger, MD, Anesth Analg, 2004, 99:1429-35.

"Neuro Research & Development" printed Jul. 18, 2008, http://www.i-biomed.com/page_files/Page847.htm, p. 1.

Ripple, LLC—innovative neurotechnology "current projects in development," printed Jul. 18, 2008, http://www.rppl.com/html/indevelopment.html, pp. 1-3.

TECH-Net Award Detailed Information, "Automated Seizure Detection Following Nerve Agent Exposure," last updated Aug. 3, 2007, http://tech-net.sba.gov/tech-net/public/dsp_award.cfm?IMAwrdSeqNmb=80205, p. 1.

TECH-Net Award Detailed Information, "Surgical Monitor for Detection of Spinal Cord Injury," last updated Aug. 3, 2007, http://tech-net.sba.gov/tech-net/public/dsp_award.cfm?IMAwrdSeqNmb=66713, p. 1.

\* cited by examiner

FLEXIBLE HEADSET FOR SENSING BRAIN ELECTRICAL ACTIVITY

TECHNICAL FIELD

The present disclosure relates to a flexible headset, and specifically, to a flexible headset for sensing brain electrical activity.

BACKGROUND

The central nervous system (CNS), and the brain in particular, perform some of the most complex and essential processes in the human body. In many cases, however, contemporary health care lacks sophisticated tools to objectively assess brain function. A patient's mental and neurological status is typically assessed clinically by an interview and a physical exam. A typical clinical laboratory currently has no capacity to assess brain function or pathology.

Brain imaging technologies, such as computed tomography imaging (CT), magnetic resonance imaging (MRI), positron emission tomography (PET), and single photon emission computerized tomography (SPECT) are widely used and useful, however, these technologies are limited in their ability to provide information about brain function, especially at the early stages of acute care situations. These limitations may be especially significant after trauma has occurred because the brain can require immediate attention to avoid further deterioration.

Many current imaging technologies, when used immediately following an acute brain injury, stroke, diffuse axonal injury (DAI), or seizure, may not reveal any abnormality in the brain even when there is dramatically abnormal brain function. CT and MRI may only detect the condition after the morphology or structure of the brain has changed. In some cases it can take from hours to days after the patient is present in an emergency room (ER) before overt changes are evident on the CT or MRI, and before severe neurological pathology is visible. Electrical activity of the brain, however, is affected immediately.

All of the brain's activity, whether reflexive, automatic, unconscious, or conscious, is electrical in nature. Through a series of electrochemical reactions, mediated by molecules called neurotransmitters, electrical potentials (voltages) are generated and transmitted throughout the brain, traveling continuously between and among a myriad of neurons. This activity establishes the basic electrical signatures of the electroencephalogram (EEG) and creates identifiable frequencies that have a basis in anatomic structure and function. Understanding these basic rhythms and their significance makes it possible to characterize the EEG as being within or beyond normal limits. At this basic level, the EEG serves as a signature for both normal and abnormal brain function.

The electrical activity of the brain has been studied extensively for decades, and especially since the advent of computers. "Normal" electrical activity of the brain has been well characterized in hundreds of studies, with a narrow standard deviation. The electrical activity of some parts of the brain that is a normal response to certain stimuli, such as acoustic, visual, or sensory stimuli, is known as an "evoked potential." Evoked potentials (EP) are particular waves that have characteristic shapes, amplitudes, durations of peaks within the wave shapes, and many other features, all of which have well established normative data generated over decades of research. Normative data for all of the EEG and evoked response waves are remarkably constant across different genders, ages, and ethnicities. Moreover, any variability that does exist is well described and explained.

Neuroscientists have also characterized the EEG signature of various different brain pathologies. Just as an abnormal electrocardiogram (ECG) pattern is a strong indication of a particular heart pathology, an irregular brain wave pattern is a strong indication of a particular brain pathology. A wide array of pathologies have been well characterized: acute and chronic, structural, toxic, metabolic, and even specific diagnoses such as: ischemic stroke, epileptic seizures, concussion, alcohol, and drug overdose, psychiatric conditions, and dementias including Alzheimer's disease. A large body of data, with continuing refinements and contributions, constitutes the field of clinical neurophysiology.

Even though EEG-based neurometric technology is accepted today and a tremendous body of data exists, application in the clinical environment is notably limited. For example, standard EEG equipment includes an array of electrodes that is placed onto the scalp of a patient. The array usually includes 19 or more electrodes that are placed directly onto the scalp of the patient (often with a conductive gel or paste) or fitted onto the patient using a cap or net. Applying the array of electrodes, each with its own lead wire, can be tedious and time consuming. The wires of the electrodes can also easily become tangled and may interfere with other operations. Furthermore, some equipment used for evoking potentials (e.g., strobe lights, etc.) may be too bulky or may be inappropriate for certain situations. Thus, current EEG equipment and electrode arrays are often not practical for the ER, operating room (OR), intensive care unit (ICU), first response situations, sporting events, or other settings and situations.

The current disclosure is directed to overcoming one or more of the aforementioned problems.

SUMMARY

Consistent with the present disclosure, there is provided a headset for detecting brain electrical activity. The headset may include a flexible band having a first end and a second end. The flexible band may include at least one expansible region permitting a distance between the first end and the second end to selectably vary. The headset may also include flexible circuitry in the flexible band. The flexible circuitry may be operatively connected to at least one sensor configured to sense brain electrical activity. The headset may further include a stimulus emitter coupled to the flexible band.

The present disclosure provides for another headset for detecting brain electrical activity. The headset may include a flexible band having a first end and a second end. The flexible band may include at least one expansible region permitting a distance between the first end and the second end to selectably vary. The headset may also include flexible circuitry in the flexible band. The circuitry may be operatively connected to at least one sensor configured to sense brain electrical activity. The headset may further include at least two securing devices coupled to the flexible band, wherein the at least two securing devices are configured to secure the headset in place by anchoring to a subject's ears.

The present disclosure additionally provides for a device for detecting brain electrical activity. The device may include a base unit. The device may also include a headset that communicates with the base unit. The headset may include a band composed of flexible material, the band including at least one expansible region. The headset may also include flexible circuitry in the band, the flexible circuitry including at least one sensor. The headset may further include a stimulus emitter coupled to the band.

The present disclosure also provides for a headset for detecting brain electrical activity. The headset may include a band composed of stretchable material. The band may have a first end and a second end. The band may permit a distance between the first end and the second end to selectably vary. The headset may also include flexible circuitry integrated into the band and operatively connected to at least one sensor configured to sense brain electrical activity.

The present disclosure provides for another headset for detecting brain electrical activity. The headset may include a flexible band having a first end and a second end. The flexible band may include at least one expansible region permitting a distance between the first end and the second end to selectably vary. The headset may be composed of an electrically conductive material. The headset may also include at least one sensor associated with the headset and configured to sense brain electrical activity.

It is to be understood that both the foregoing general description and the following detailed description are exemplary and explanatory only and are not restrictive of the claims.

The accompanying drawings, which are incorporated in and constitute a part of this specification, illustrate embodiments consistent with the present disclosure.

DETAILED DESCRIPTION

Figure 1:
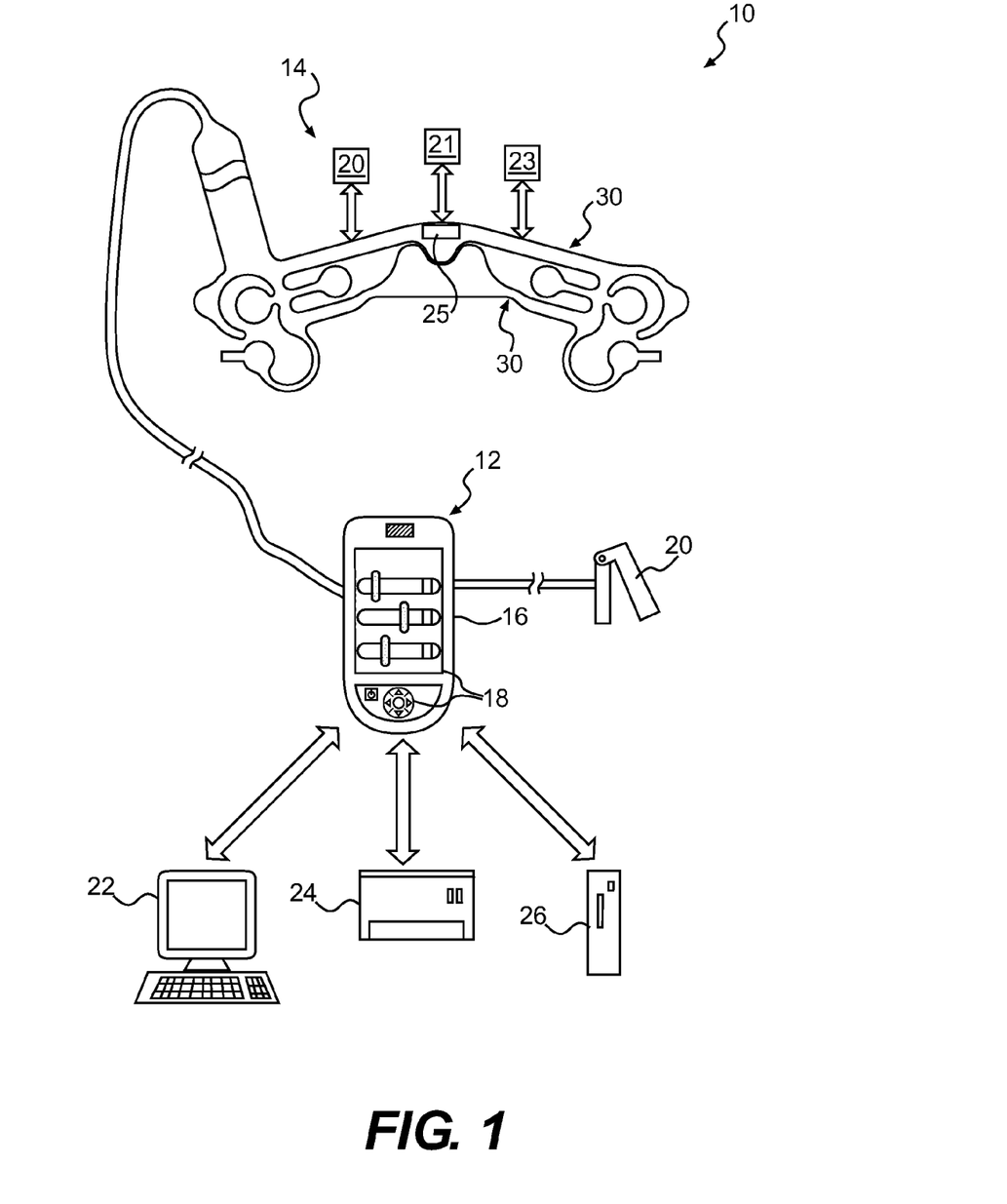
FIG. 1 shows an exemplary embodiment of the disclosed Bx™ brain assessment system.

FIG. 1 shows a Bx™ brain assessment system 10. Brain assessment system 10 may be configured to assess a brain-state of a patient or subject and may include a base unit 12, which can be handheld, and a headset 14 configured to communicate brain electrical activity with base unit 12. In one embodiment, headset 14 and base unit 12 may come in a kit. The kit may be designed for performing neurological triage of a patient. The kit may include instructions for using base unit 12 and a portable carrying case.

Base unit 12 may be a device configured to analyze, communicate, save, and/or display brain electrical activity data. Base unit 12 may be sized to fit in one's hand. Base unit 12 may include a display 16, such as an LCD screen. Base unit 12 may also include and a user interface 18. User interface 18 may embody, for example, a touch screen interface, a keyboard, a voice activated interface, or any other user interface known in the art. In one embodiment, base unit 12 may include a pulse oximeter 20 for monitoring the patient's pulse and blood oxygen levels.

Base unit 12 may contain appropriate hardware for analyzing, communicating, saving, and/or displaying data. For example, base unit 12 may include a processor, a memory, a power source (e.g., a battery), and a multi-channel input/output interface. Base unit 12 may also include signal amplification circuitry, signal filtering circuitry, A/D conversion circuitry, and/or any other appropriate circuitry known in the art. The data received and analyzed by base unit 12 may include signals indicative of brain electrical activity received from headset 14.

Base unit 12 may also include appropriate software. Base unit 12 may include, for example, a graphical user interface (GUI) and an analysis application designed to analyze brain electrical activity data. It is contemplated that the analysis application may use one or more algorithms to extract and/or organize key signal features of the brain data to identify and classify brain dysfunctions. The dysfunctions may include, for example, seizure, ischemic stroke, elevated intracranial pressure, hematoma, concussion/contusion, dementia, and depression. The algorithms may use fractal mathematics and nonlinear signal processing to identify and classify brain electrical signals to aid in diagnosis of brain states or conditions.

Base unit 12 may communicate with headset 14 via one or more communications lines and/or wirelessly. Base unit 12 also may communicate via communication lines and/or wirelessly with an external computer 22, a printer 24, or an external memory 26 (e.g., external hard drive, flash-memory device, optical drive, floppy drive, or any other non-volatile memory). It is contemplated that the wireless capabilities between base unit 12 and other components of brain assessment system 10, including headset 14, may be short range (e.g., Bluetooth®, Wi-Fi, IR, etc.) and/or long range (e.g., cellular, satellite, etc.).

Headset 14 may include a plurality of sensing devices, such as a pulse oximeter 20, a temperature sensor 21, and a near infra-red spectroscopy device 23. It is contemplated that pulse oximeter 20 associated with headset 14 may have at least two wavelengths or more. Temperature sensor 21 may embody a thermocouple, a resistive sensor, or any other type of temperature sensor known in the art. Near infra-red spectroscopy device 23 may include a CCD or thermal camera. It is contemplated that pulse oximeter 20, temperature sensor 21, and near infra-red spectroscopy device 23 may be integrated into a band potion 30 of headset 14, or alternatively, may be independent units connected to headset 14 via communication lines or via wireless means. In one embodiment, near infra-red spectroscopy device 23 may be a small unit tethered to headset 14 that can be applied to the subject's scalp.

Headset 14 may also include a display 25. Display 25 may embody a LCD display or an LED strip. It is contemplated that display 25 may display results of analysis, senor readings, or other information received from base unit 12.

Figure 2A:
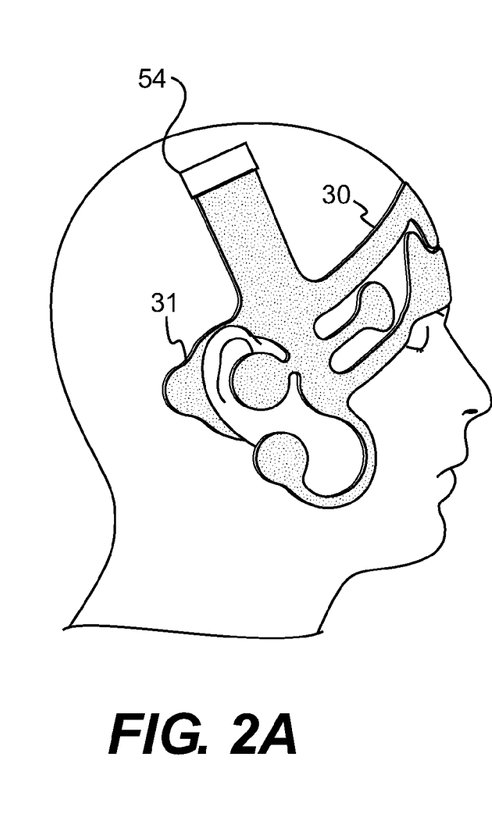
FIGS. 2A, 2B, and 2C show a headset that may be used with the brain assessment system of FIG. 1.
Figure 2B:
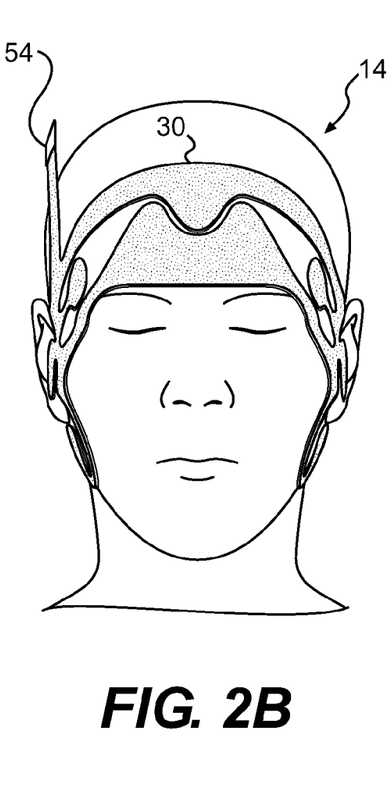
Figure 2C:
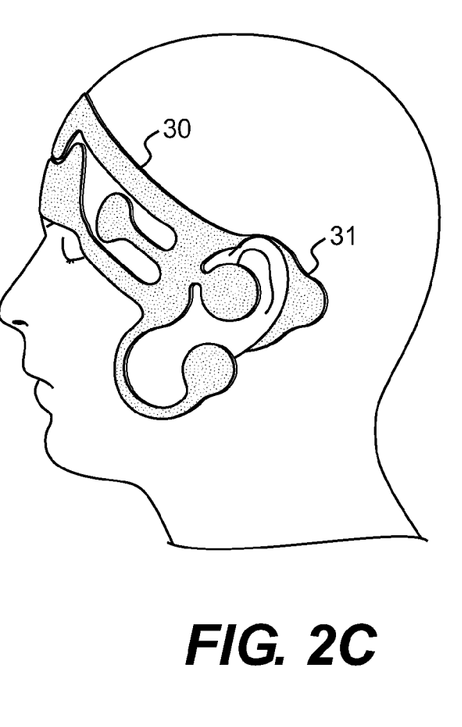

As shown in FIGS. 2A, 2B, and 2C, headset 14 may be a device configured for use on the head of a human patient. It is contemplated that headset 14 may also be used with other mammalian subjects. Headset 14 may include two securing devices 31. One securing device 31 may be located at a first end of band portion 30 and the other securing device 31 may be located at a second end of band portion 30. Band portion 30 may be placed on or affixed to the forehead of the subject. Each securing device 31 of headset 14 may fit behind an ear of the subject and anchor to the ear of the subject, thus securing band portion 30 to the forehead of the subject. Headset may also include a connector 54 that allows communication between headset 14 and base unit 12. It is contemplated that headset 14 may be a disposable or a reusable device.

Figure 3:
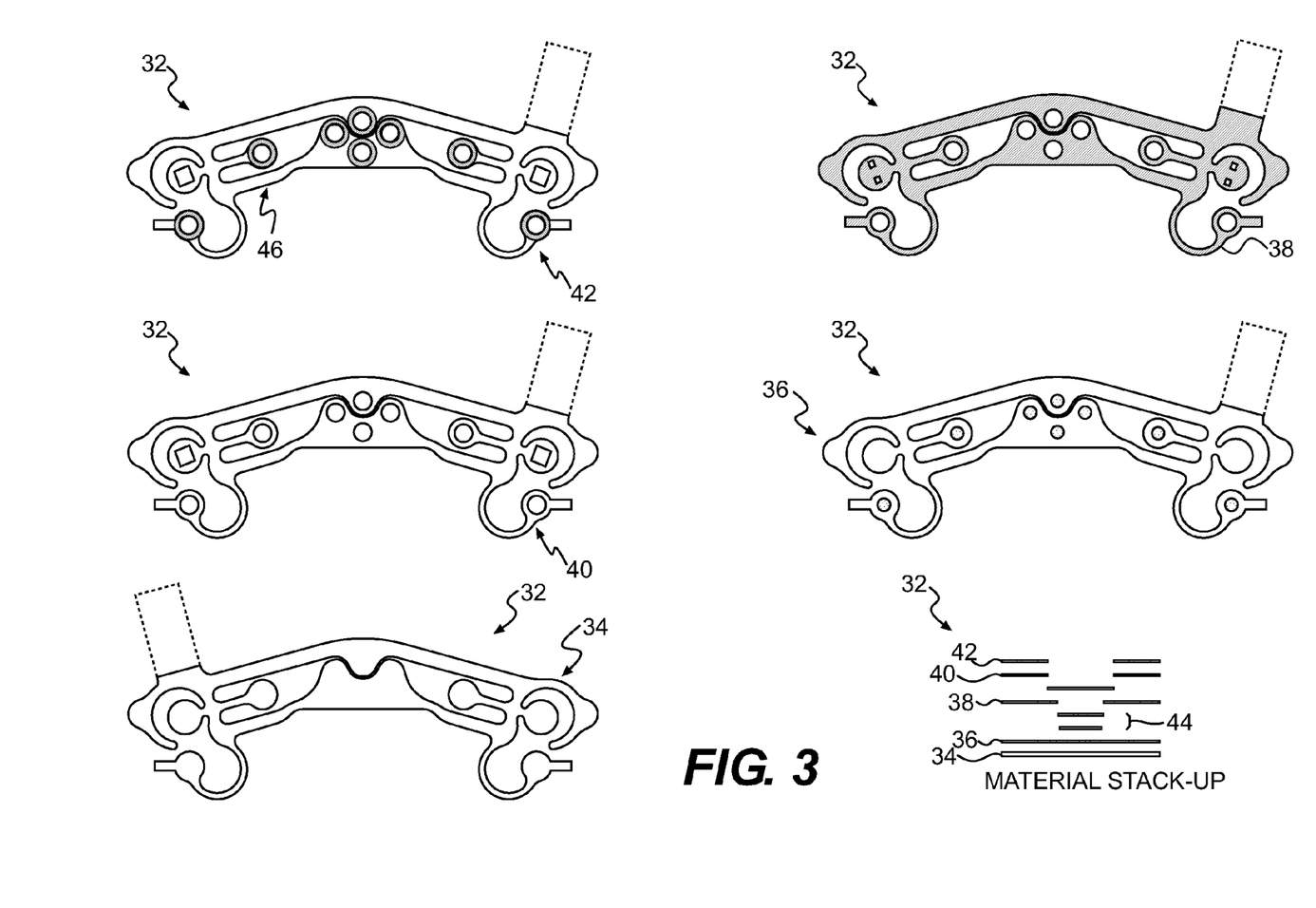
FIG. 3 shows a plurality of layers that may comprise the headset of FIG. 2.

As shown in FIG. 3, headset 14 may be composed of one or more layers 32. It is contemplated that each layer 32 may be composed of a flexible material to allow headset 14 to conform to varying head geometries. All layers may be flexible to allow for use on subjects having heads of varying diameter. For human subjects, it is contemplated that adult and pediatric sizes may be available, for example. Layers 32 may include, for example, an outer layer 34, a substrate layer 36, a dielectric layer 38, an inner layer 40, and an adhesive layer 42.

Outer layer 34 may provide protection and/or support for headset 14. It is contemplated that outer layer 34 may be composed of medical foam, plastic, flexible composite, or other materials known in the art. Outer layer 34 may attach to substrate layer 36 in any appropriate manner, such as chemical or mechanical bonding (e.g., rivet, adhesive, etc.).

Substrate layer 36 may be the layer upon which circuitry 44 (see FIG. 4) of headset 14 is located. Substrate layer 36 may be composed of polyamide (e.g., Kapton®), polyester, aramid, or any other flexible substrate material. It is contemplated that circuitry 44 may be printed, etched, or bonded onto substrate layer 36. Circuitry 44 (see FIG. 4) may be composed of an electrically conductive material, such as, for example, copper, silver, silver-chloride, gold, tin, or any other conductive material or combination of materials known in the art. Circuitry 44 may also include any appropriate finish known in the art. Substrate layer 36 and circuitry 44 may be covered by dielectric layer 38.

Dielectric layer 38 may cover and help electrically insulate circuitry 44. Dielectric layer 38 may be composed of polyamide, polyester, aramid, or other dielectric composites or materials known in the art. Dielectric layer 38 may be bonded to substrate layer 36 and circuitry 44 using, for example, heat and/or adhesive bonding. Dielectric layer 38 may alternatively embody a cover coat that is screen printed and cured onto substrate layer 36 and circuitry 44.

Inner layer 40, similar to outer layer 34, may provide protection and/or support for headset 14. It is contemplated that inner layer 40 may be composed of medical foam, plastic, flexible composites, or other materials known in the art. Inner layer 40 may attach to dielectric layer 38 in any appropriate manner, such as chemical or mechanical bonding (e.g., rivet, adhesive, etc.).

An adhesive layer 42 may be applied to an exterior side 46 (i.e., side that contacts a subject's forehead) of inner layer 40. Adhesive layer 42 may cover all of exterior side 46, or alternatively, only discrete portions of exterior side 46. Adhesive layer 42 may allow headset 14 to attach and adhere to the forehead of a subject. It is contemplated that adhesive layer 42 may embody any appropriate medical adhesive, such as, for example, a silicon or synthetic rubber adhesive on a double sided medical tape. Exterior side 46 of adhesive layer 42 may be covered with a removable protective paper or covering. The paper or covering may protect adhesive layer 42 until headset 14 is applied to a subject.

It is contemplated that one or more of layers 34, 36, 38, and 40 may alternatively be composed of a stretchable material. The stretchable material may include, for example, rubber, silicone, or polyurethane. It is further contemplated that circuitry 44 may utilize, for example, a meandering configuration in order to accommodate the use of stretchable materials.

Headset 14 may also be composed of one or more electrically conductive materials, such as, for example, conductive fibers. The conductive fibers may be rigid or flexible.

Figure 4:
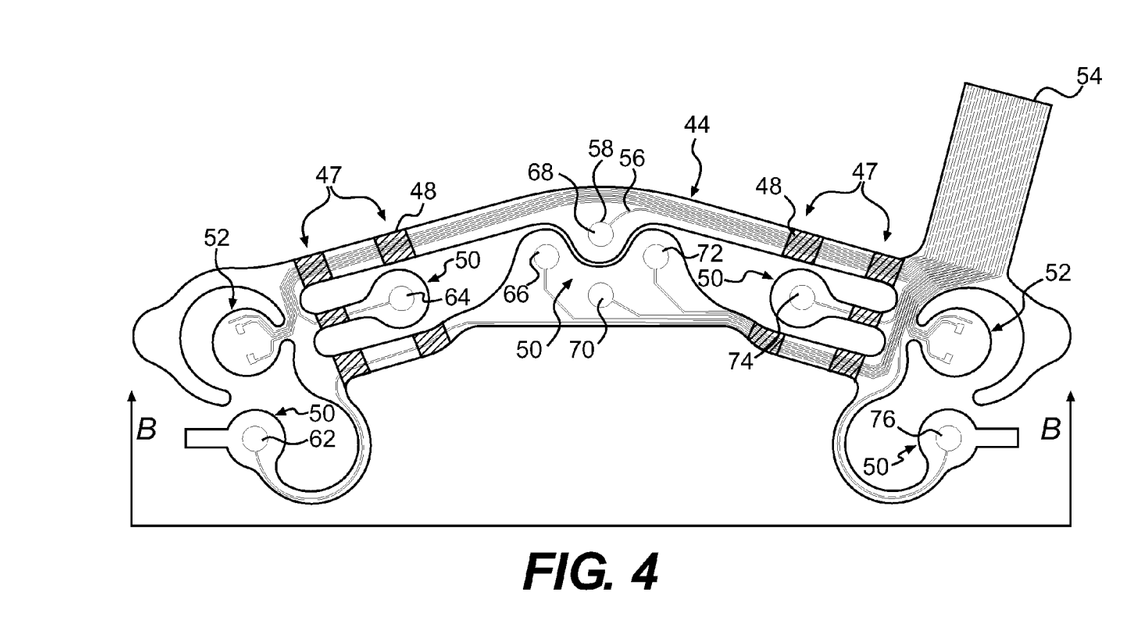
FIG. 4 shows exemplary circuitry that may be included in the headset of FIG. 2.
Figure 5:
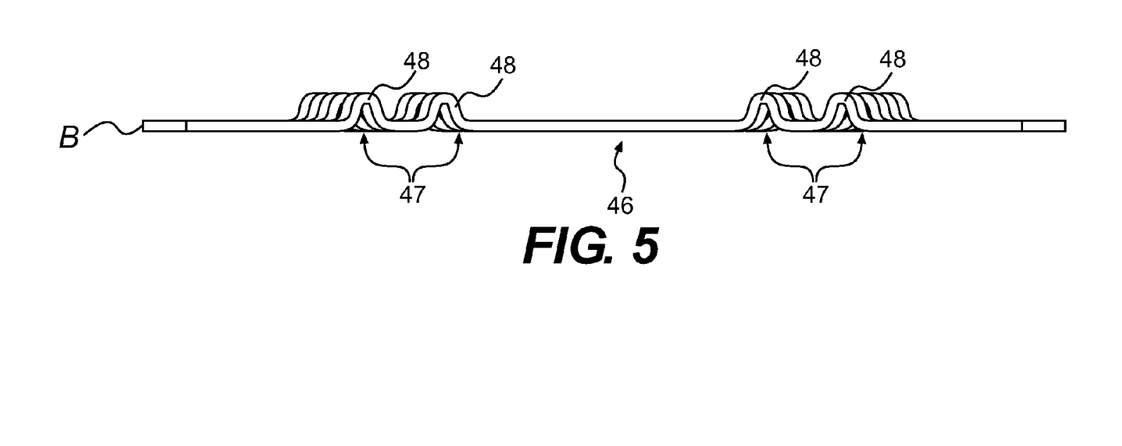
FIG. 5 shows another view of the headset of FIG. 4.

As shown in FIGS. 4 and 5, headset 14 may include features, such as expansible regions 47, that allow headset 14 to fit a wide range of subject head geometries. Expansible regions 47 may be regions of headset 14 that allow expansion and/or contraction of headset 14 in its longitudinal dimension (i.e., allows a distance between the first and second ends of band portion 30 to selectably vary). In one embodiment, expansible regions 47 may embody flexures or corrugations 48 in headset 14. When a longitudinal tensile force is applied to headset 14, each flexure or corrugation 48 may expand, thus allowing headset 14 to increase its length to accommodate a given head geometry. Similarly, a compression force may cause flexures or corrugations 48 to contract and reduce the length of headset 14. Expansible regions 47 may also embody a serpentine, a meandering, or a zig-zag construction. Layers 32 and circuitry 44 may be composed of generally flexible materials so that headset 14 can conform to various head geometries. A better and closer fit of headset 14 to various head geometries may improve subject comfort and signal quality of the sensed brain electrical activity.

Headset 14 may also be configured to stimulate and/or sense brain electrical activity data of a subject. As shown in FIG. 4, headset 14 may include circuitry 44. Specifically, headset 14 may include a plurality of sensors 50, a stimulus emitter 52, and a connector 54.

Sensors 50 may be devices configured to sense brain electrical activity. For example, sensors 50 may embody electrodes configured to sense electrical currents created by synaptic potentials. Each sensor 50 may include an electrically conductive trace 56 that attaches to connector 54. It is contemplated that a terminal end of each sensor 50 may include a node 58. Each node 58 may embody, for example, a substantially flat metallic disc. Node 58 and conductive trace 56 may be composed of any appropriate electrically conductive material, such as, for example, copper, silver, gold, tin, or any other appropriate material known in the art. In one embodiment, one or more of sensors 50 may be disposable while the remaining portion of headset 14 may be reusable.

In an illustrative embodiment, sensors 50 may include a right peripheral sensor 62, a right temple sensor 64, a right forehead sensor 66, an upper middle forehead sensor 68, a lower middle forehead sensor 70, a left forehead sensor 72, a left temple sensor 74, and a left peripheral sensor 76. It is contemplated that any of sensors 50 may be a ground. Peripheral sensors 62 and 76 may be configured to be located at the subject's earlobes (i.e., left and right earlobe sensor) or mastoids (i.e., left and right mastoid sensor). It is further contemplated that sensors 50 may include two sets of peripheral sensors 62 and 76, one set configured to be located at the subject's earlobes, and one set configured to be located at the subject's mastoids.

Stimulus emitter 52 may be a device configured to evoke a response from the subject. Stimulus emitter 52 may embody, for example, a piezoelectric transducer or a speaker. Stimulus emitter 52 may be configured to be located at, in, over, or near a subject's ear. Base unit 12 may send a signal to stimulus emitter 52 that causes stimulus emitter 52 to produce an auditory stimulus. The auditory stimulus may evoke a response from the brain of the subject that is recorded using headset 14. It is contemplated that other stimulus emitters may additionally or alternatively be used with headset 14, such as, for example, visual devices, sensory devices, or other devices known in the art.

Connector 54 may allow headset 14 to connect and communicate with base unit 12. Specifically, connector 54 may allow signals to be communicated between base unit 12 and sensors 50. Connector 54 may also allow signals to be communicated between base unit 12 and stimulus emitter 52. In one embodiment, connector 54 may be a male or female-type connector that mates to a connector of base unit 12. It is contemplated that connector 54 may alternatively embody a wireless connector, such as, for example, an RF antenna or an IR emitter/receiver.

Figure 6:
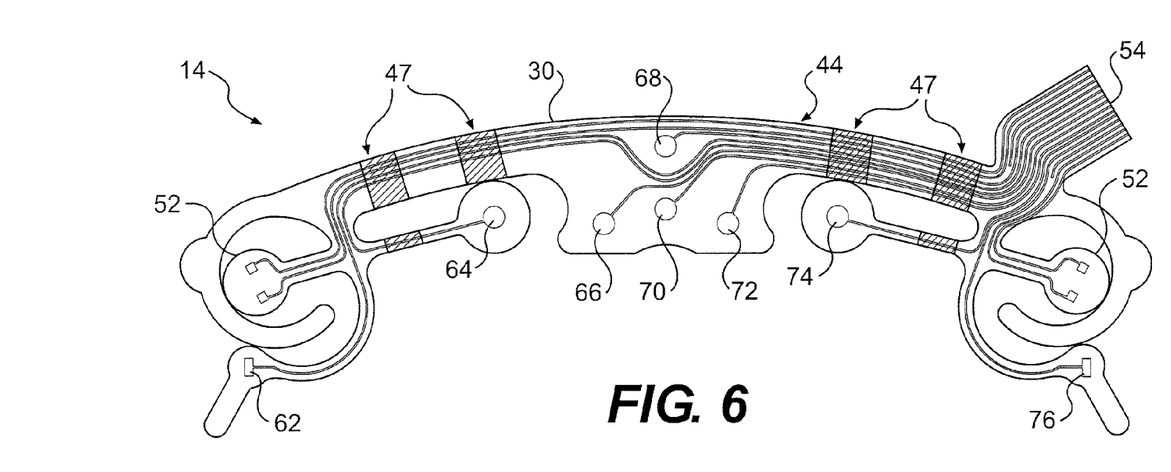
FIG. 6 shows another embodiment of the headset, including exemplary circuitry.

FIG. 6 shows an additional embodiment of headset 14. It is contemplated that the embodiment shown in FIG. 6 may include all or substantially all of the components of the embodiment of headset 14 shown in FIGS. 1-5.

Figure 7:
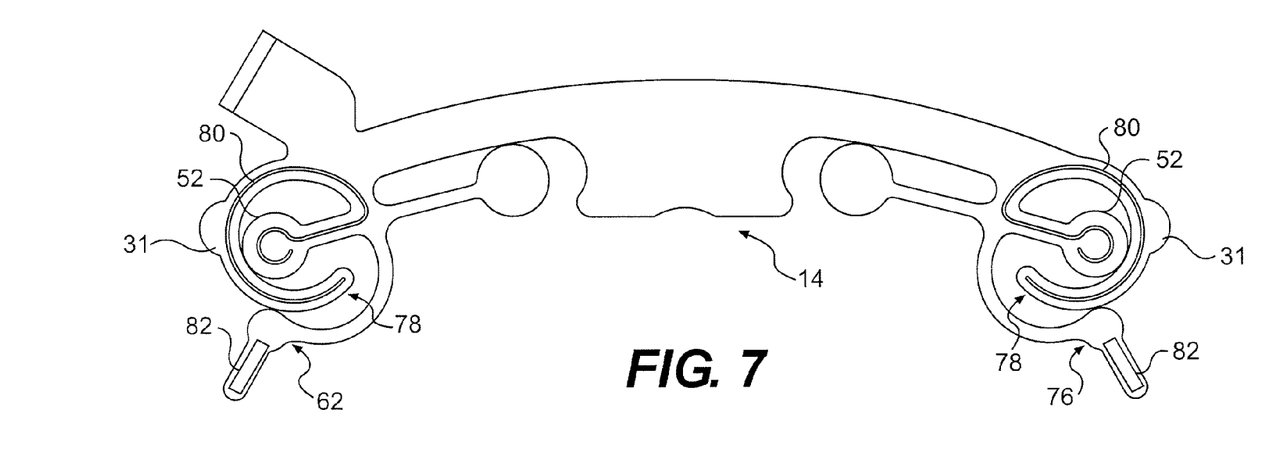
FIG. 7 shows strengthening members that may be used with the headsets of FIGS. 1-6.

As shown in FIG. 7, headset 14 may also include strengthening members 78. Headset 14 may include a first strengthening member 80 and a second strengthening member 82. Strengthening members 78 may be embedded between layers 32 (e.g., between outer layer 34 and substrate layer 36) or within layers 32.

As shown in FIG. 7, each first strengthening member 80 may embody a single continuous band or wire that passes through securing device 31 and terminates near the end of stimulus emitter 52 (it is contemplated that each first strengthening member 80 may alternatively comprise multiple segments). First strengthening member 80 may be configured to reinforce securing device 31. First strengthening member 80 may also allow for stimulus emitter 52 to be securely positioned over the subjects ear canal. For example, first strengthening member 80 may be composed of a resilient material in order to securely position stimulus emitter 52 over the subjects ear canal when headset 14 is in position. Alternatively, first strengthening member 80 may be composed of a deformable material that allows for first strengthening member 80 to be positioned over the subject's ear canal. First strengthening member 80 may be composed of plastic, metal, or any other appropriate material known in the art. In one embodiment, first strengthening member 80 may be composed of an aluminum wire.

Each second strengthening member 82 may embody a thin tab located in headset 14 at or near left and right peripheral sensors 62 and 76. Second strengthening member 82 may be composed of plastic, metal, or any other appropriate material known in the art. In one embodiment, second strengthening member 82 may embody a thin aluminum tab. Since each second strengthening member 82 may be composed of rigid yet deformable material, each second strengthening member 82 may be folded around the back of the subject's earlobes in order to secure left and right peripheral sensors 62 and 76 to the subject's ears.

Figure 8:
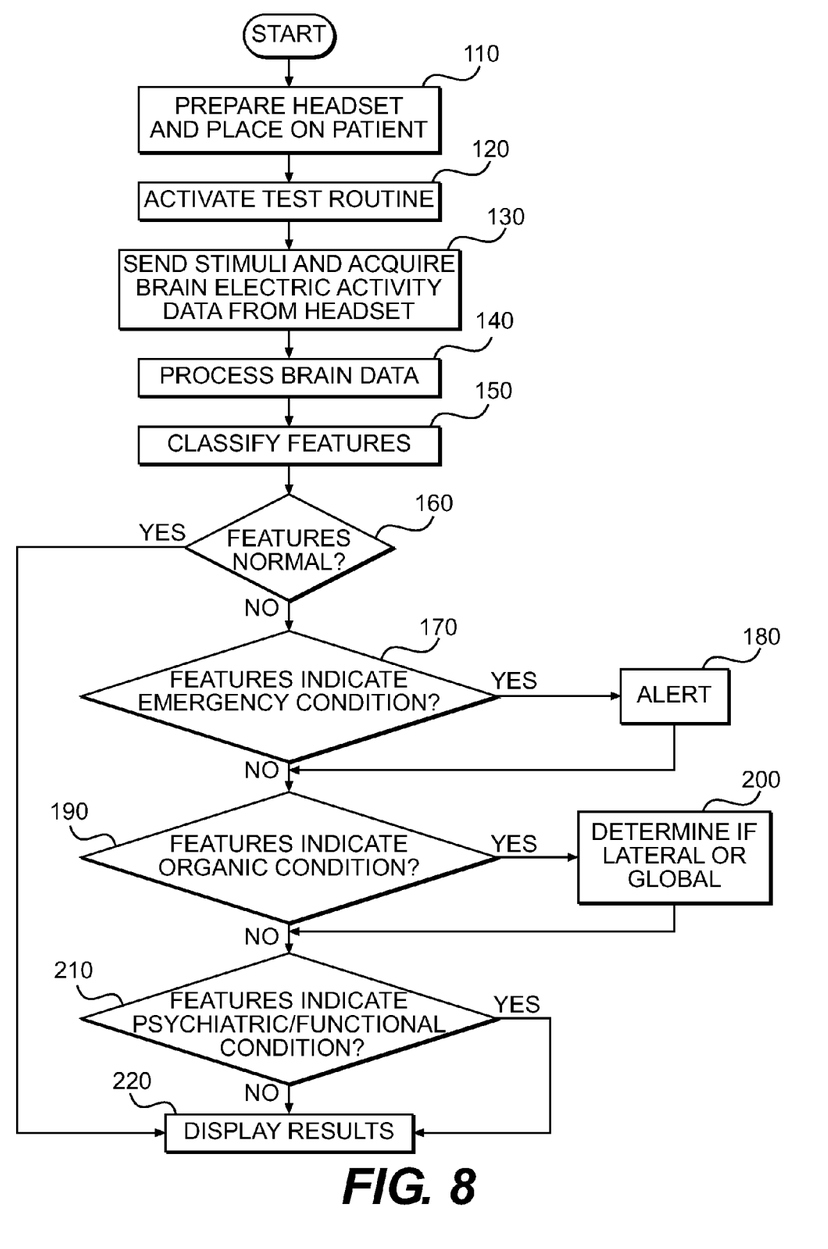
FIG. 8 shows an exemplary method for use of the brain assessment system of FIG. 1.

FIG. 8 shows an exemplary operation and use of brain assessment system 10, which is further described in U.S. patent application Ser. No. 11/195,001, which is incorporated by reference herein in its entirety. Prior to placing headset 14 on the subject, the protective paper or covering may be removed from adhesive layer 42. Headset 14 may then be placed on the forehead of the subject (step 110), allowing adhesive layer 42 to adhere to the forehead of the subject. Each securing device 31 may be placed behind an ear of the subject. It is contemplated that the placing securing devices 31 behind the ears of the subject may cause expansible regions 47 to stretch or compress as necessary to accommodate the head geometry of the subject. Furthermore, the flexible materials used in the manufacturing of layers 32 may allow headset 14 to conform to the head geometry of the subject.

Headset 14 may then be connected to base unit 12 (if not already connected). The connection may involve a physical connection and/or a wireless connection between headset 14 and base unit 12. After connection, a command entered through user interface 18 may begin a test routine (step 120). The test routine may involve base unit 12 sending a signal to stimulus emitter 52 to produce a stimulus (step 130). The stimulus may embody, for example, an auditory stimulus produced using a piezoelectric speaker. It is contemplated that the auditory stimulus may be given to the subject to obtain an Auditory Evoked Potential (AEP). The Auditory Evoked Potentials may comprise auditory brainstem response (ABR) potentials, auditory mid-latency response (AMLR) potentials, and/or auditory late response (ALR) potentials, including P100 responses, and P300 responses. Before, after, and/or during the activation of stimulus emitter 52, base unit 12 may communicate with headset 14 to gather brain electrical activity data (step 130). The brain electrical activity data may include the evoked response to the stimulus, spontaneous activity, or a combination thereof.

The brain electrical activity data may be processed (step 140) using the hardware and software of base unit 12. During processing, artifacts may be removed from the data. Artifacts may be a result of such factors as a disconnected electrode, electromyogram (EMG) artifacts resulting from muscular movement, eye movement, and other significant artifacts. In one embodiment, the artifacts may be removed by removing discrete artifact sections from the signals. In another embodiment, the artifacts may be removed by subtracting out any artifacts present in the acquired signals.

The artifact-free signals may be further processed by extracting statistical signal features. In one embodiment consistent with the present invention, a quantitative EEG algorithm may be used to extract features. In another embodiment, a wavelet packet algorithm may be used for feature extraction. In a further embodiment, spectral analysis and statistical procedures may be performed to extract features. In yet a further embodiment, diffusion geometric analysis may be performed to extract features. In yet another embodiment, microstate analysis may be performed to extract features. In a further embodiment, wavelet-packet local discriminant basis algorithms may be applied to extract features.

The extracted features may be classified according to one or more diagnostic categories (step 150). During classification, a probability that features extracted from a subject can be classified in one or more diagnostic categories is determined. Classifying may be performed by applying discriminant analysis to the extracted features, or by applying wavelet-packets to the extracted features.

Brain assessment system 10 may then determine if the results are normal (step 160). If the features extracted from the subject's brain waves are normal, then the device may display that the subject's brain activity is normal (step 220). If there is a higher probability that the subject's extracted features are not normal, brain assessment system 10 may determine if the extracted features can be classified as an emergency or "Alert" condition (step 170). An emergency condition may include a brainstem dysfunction, seizure, stroke, DAI, or elevated intracranial pressure. If there is a high probability that an emergency condition exists, brain assessment system 10 may alert the user (step 180). Brain assessment system 10 may alert the user using any appropriate audio, visual, or sensory means (e.g., flashing light, flashing text, buzzer, vibration, wireless transmission to other device, etc.).

Brain assessment system 10 may determine if the abnormality of the extracted features appears to be organic in nature (step 190). If the extracted features are determined to correlate with an extracted feature abnormality that is organic in nature, the device may then attempt to determine if the extracted feature abnormality is lateral or global in nature (step 200). Brain assessment system 10 may also determine if the extracted features have a high probability of indicating a psychiatric or "functional" problem (step 210).

Base unit 12 may output results concerning the assessment of subject's brain in accordance with the classification (step 220). It is contemplated that brain assessment system 10 may output the results in real time. Output may be displayed on display 16, saved to internal or external memory 26, displayed or saved to external computer 22, and/or printed using printer 24. It is contemplated that the probability that the subject belongs to a particular diagnostic category can be displayed on display 16. For example, in a scenario where the subject is most likely exhibiting an organic, lateral abnormality, display 16 may display, for example, that subject's brain function is 80% indicative of a hemorrhagic stroke, 15% indicative of an ischemic stroke, and 5% of a subdural hematoma.

It is contemplated that base unit 12, or components thereof (e.g., processor, display 16, user interface 18, etc.), may be located on headset 14. Thus, although shown as two separate units, base unit 12 and headset 14 may be integrated into a single headset unit with an onboard power source (e.g., a battery). It is also contemplated that headset 14 may include a chip with code such that base unit 12 may identify and authenticate headset 14 upon or after connection to base unit 12. The chip may include, for example, a unique identifier.

The disclosed brain assessment system and method may provide several advantages. Specifically, the flexible and expandable design of the disclosed headset may allow for quick and easy placement of the headset on a wide array of subject head geometries. Furthermore, the flexible materials used in the disclosed headset may allow the headset to conform more closely to the subject's head, thus improving sensor measurements. The disclosed headset may also include a "built-in" stimulus device allowing for easy measurement of evoked potentials in a variety of situations (e.g., emergency room, ICU, sporting events), thus helping improve diagnosis and care for victims of head injury and neurological maladies.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for detecting brain electrical activity of a subject, the device comprising:
   a base unit; and
   a headset that communicates with the base unit, the headset including:
     a flexible band having a first end, a second end, and a center portion;
     a first and a second securing device respectively adjacent to the first and second ends of the flexible band;
       wherein the band includes a first expansible region between the first end and the center portion, and a second expansible region between the second end and the center portion, and wherein the first and the second expansible regions are configured to adaptively stretch or contract to accommodate different forehead sizes when the first and the second securing devices are anchored to the subject's ears;
     flexible circuitry in the band, the flexible circuitry including at least one sensor; and
     a stimulus emitter coupled to the band; and
       further wherein the headset is configured to automatically place the at least one sensor in an accurate position on the forehead when the first and the second securing devices are anchored to the subject's ears.

2. The device of claim 1, wherein the stimulus emitter includes one or more piezoelectric transducers.

3. The device of claim 1, wherein the first and the second expansible regions each include a flexure or corrugation in the band.

4. The device of claim 1, wherein the at least one sensor includes a right temple region sensor, a right forehead sensor, an upper middle forehead sensor, a lower middle forehead sensor, a left forehead sensor, and a left temple region sensor.

5. The device of claim 4, wherein the at least one sensor includes at least one of a right mastoid sensor, a left mastoid sensor, a right earlobe sensor, or a left earlobe sensor.

6. The device of claim 1, wherein the base unit includes:
   a pulse oximeter;
   a user interface configured to receive user commands;
   software and hardware configured to analyze brain electrical activity data received from the at least one sensor; and
   a display configured to display results from the data analysis.

7. The device of claim 1, wherein the base unit is a handheld unit.

8. The device of claim 1, wherein the base unit is configured to communicate with at least one of an external computer, a printer, or an external memory.

9. The device of claim 1, wherein the headset includes a chip with a unique identifier.

10. The device of claim 1, wherein the base unit is integrated into the headset, and wherein the base unit and the headset are powered by an onboard battery.

11. A headset for detecting brain electrical activity of a patient, comprising:
    a flexible band having a first end, a second end, and a center portion;
    a first sensor coupled to the center portion and configured to sense brain electrical signals;
    a second sensor coupled adjacent to one of the first end or the second end and configured to sense brain electrical signals; and
    securing devices located at the first end and the second end; and
    flexible circuitry in the flexible band, the flexible circuitry operatively connected to the first and second sensor;
      wherein the flexible band includes a first expansible region adjacent to the first end and a second expansible region adjacent to the second end permitting a distance between the first end and the second end to selectably vary with respect to the center portion; and
      further wherein the flexible band is configured to automatically place the second sensor in an accurate position on the forehead of the patient, without any manual adjustment of the first expansible region or the second expansible region, by locating the securing devices behind the patient's ears.

12. The headset of claim 11, wherein at least one of the first and the second expansible regions are configured to stretch or compress when the securing device are located behind the patient's ear.

13. The headset of claim 11, wherein the band is composed of two or more layers, each layer comprising a flexible material.

14. The headset of claim 11, further including a stimulus emitter coupled to the flexible band.

15. The headset of claim 14, wherein the stimulus emitter is a piezoelectric transducer.

16. The headset of claim 11, wherein at least one of the first and the second expansible regions include a flexure or corrugation in the flexible band.

17. The headset of claim 11, further including an adhesive layer located on an exterior side of the headset configured to secure the flexible band to a patient's forehead.

18. The headset of claim 11, further including a connecter, wherein the connecter is configured to communicate with a base unit, the base unit including software and hardware configured to analyze brain electrical activity data received from the first and the second sensor.

19. The headset of claim 11, wherein the first sensor includes at least one of a right forehead sensor, an upper middle forehead sensor, a lower middle forehead sensor, or a left forehead sensor.

20. The headset of claim 11, wherein the second sensor includes at least a right temple region sensor, and a left temple region sensor.

21. The headset of claim 11, wherein the flexible band is composed of a stretchable material.

22. The headset of claim 21, wherein the stretchable material includes at least one of rubber, silicone, or polyurethane.

23. A headset for detecting brain electrical activity of a patient, the headset comprising:
a flexible band having a first end, a second end, and a center portion, wherein the flexible band includes a first expansible region positioned between the first end and the center portion, and a second expansible region located between the second end and the center portion, and further wherein at least one of the first and the second expansible region is configured to permit a distance between the first end and the second end to vary adaptively to accommodate different forehead geometries;
flexible circuitry in the flexible band, the flexible circuitry operatively connected to at least one sensor configured to sense brain electrical activity; and
a first and a second securing device connected respectively to the first and the second ends of the flexible band; and
wherein the headset is configured to automatically place the at least one sensor in an accurate position on the forehead when the first and the second securing devices are anchored to the patient's ears.

24. The headset of claim 23, further including a stimulus emitter coupled to the flexible band.

25. The headset of claim 24, wherein the stimulus emitter is a piezoelectric transducer.

26. The headset of claim 23, wherein at least one of the first and the second expansible regions are configured to automatically stretch or compress when the securing devices are anchored to the patient's ears.

27. The headset of claim 23, further including at least one strengthening member.

28. The headset of claim 27, wherein the at least one strengthening member is embedded within either of the at least two securing devices.

29. The headset of claim 28, wherein the at least one strengthening member is positioned to fold over the bottom of the patient's earlobe.

30. The headset of claim 27, wherein the at least one strengthening member is embedded in the flexible band.

31. The headset of claim 27, wherein the at least one strengthening member is composed of at least one of metal or plastic.

32. The headset of claim 23, wherein at least one of the first and the second expansible regions include one or more flexures or corrugations in the flexible band.

33. The headset of claim 32, wherein the flexible circuitry passes through the one or more flexures or corrugations.

34. The headset of claim 23, wherein the flexible band is composed of one or more layers of flexible materials including at least one of medical foam, polyamide, polyester, or aramid.

35. The headset of claim 23, further including an adhesive layer located on an exterior side of the flexible band.

36. The headset of claim 23, further including a connecter coupled to the flexible circuitry.

37. The headset of claim 36, wherein the connecter is configured to communicate via one or more communication lines with a base unit, the base unit including software and hardware configured to analyze brain electrical activity data received from the at least one sensor.

38. The headset of claim 37, wherein the headset is configured to communicate wirelessly with the base unit.

39. The headset of claim 23, wherein the at least one sensor includes a right temple region sensor, a right forehead sensor, an upper middle forehead sensor, a lower middle forehead sensor, a left forehead sensor, and a left temple region sensor.

40. The headset of claim 39, wherein the at least one sensor includes at least one of a right mastoid sensor, a left mastoid sensor, a right earlobe sensor, or a left earlobe sensor.

41. The headset of claim 23, wherein the flexible band is composed of a stretchable material.

42. The headset of claim 41, wherein the stretchable material includes at least one of rubber, silicone, or polyurethane.

43. The headset of claim 23, further including a near infrared spectroscopy device.

44. The headset of claim 43, wherein the near infrared spectroscopy device includes a thermal camera, wherein the thermal camera is adapted to be positioned near the subject's scalp.

45. The headset of claim 23, further including a temperature sensor.

46. The headset of claim 23, further including a chip with a unique identifier.

47. The headset of claim 23, further including a pulse oximeter, wherein the pulse oximeter is configured to utilize at least two wavelengths.

48. A headset for detecting brain electrical activity of a patient, comprising:
a flexible band having a first end, a second end, and a center portion, wherein the flexible band includes a first expansible region positioned between the first end and the center portion, and a second expansible region located between the second end and the center portion, and further wherein at least one of the first and the second expansible region is configured to permit a distance between the first end and the second end to vary adaptively to accommodate different forehead geometries;
flexible circuitry in the flexible band, the flexible circuitry operatively connected to at least one sensor configured to sense brain electrical activity;
a stimulus emitter coupled to the flexible band; and
an integrated display located on the flexible band; and
at least two securing devices coupled to the flexible band, wherein the at least two securing devices are configured to fit behind the patient's ears;
wherein the headset is configured to automatically place the at least one sensor in an accurate position on the patient's forehead when the first and the second securing devices are anchored to the patient's ears.

49. The headset of claim 48, wherein the integrated display embodies at least one LED strip.

50. The headset of claim 48, wherein the integrated display embodies an LCD display.

51. The headset of claim 48, wherein at least one of the first and the second expansible regions are configured to automatically stretch or compress when the securing devices are located behind the patient's ears.

52. The headset of claim 48, further including at least one strengthening member.

53. The headset of claim 52, wherein the at least one strengthening member is embedded within either of the at least two securing devices.

54. The headset of claim 48, wherein at least one of the first and the second expansible regions include one or more flexures or corrugations in the flexible band.

55. The headset of claim 48, further including a connecter coupled to the flexible circuitry, wherein the connecter is configured to communicate via one or more communication lines with a base unit, the base unit including software and hardware configured to analyze brain electrical activity data received from the at least one sensor.

* * * * *